US012558166B2

(12) United States Patent
Regensburger

(10) Patent No.: US 12,558,166 B2
(45) Date of Patent: Feb. 24, 2026

(54) METHOD AND SYSTEM FOR CREATING A NAVIGATION PLAN FOR A CATHETER WITH A ROBOT

(71) Applicant: Siemens Healthcare GmbH, Erlangen (DE)

(72) Inventor: Alois Regensburger, Poxdorf (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 914 days.

(21) Appl. No.: 17/356,917

(22) Filed: Jun. 24, 2021

(65) Prior Publication Data

US 2022/0000566 A1 Jan. 6, 2022

(30) Foreign Application Priority Data

Jul. 2, 2020 (DE) ..................... 10 2020 208 325.8

(51) Int. Cl.
| | |
|---|---|
| *A61B 34/20* | (2016.01) |
| *A61B 34/10* | (2016.01) |
| *A61B 34/30* | (2016.01) |

(52) U.S. Cl.
CPC .............. *A61B 34/20* (2016.02); *A61B 34/10* (2016.02); *A61B 34/30* (2016.02); *A61B 2034/102* (2016.02); *A61B 2034/107* (2016.02); *A61B 2034/301* (2016.02)

(58) Field of Classification Search
CPC ......... A61B 34/20; A61B 34/10; A61B 34/30; A61B 2034/102; A61B 2034/107; A61B 2034/301
See application file for complete search history.

(56) References Cited

U.S. PATENT DOCUMENTS

| | | | | |
|---|---|---|---|---|
| 6,298,257 | B1 * | 10/2001 | Hall .......................... | A61B 5/29 |
| | | | | 600/407 |
| 7,744,537 | B2 * | 6/2010 | Kanai .................. | A61B 8/0858 |
| | | | | 600/453 |
| 11,547,490 | B2 * | 1/2023 | Wang ..................... | A61B 34/10 |
| 11,925,452 | B2 * | 3/2024 | Brannan ................ | A61B 5/113 |
| 2002/0019644 | A1 | 2/2002 | Hastings et al. | |

(Continued)

FOREIGN PATENT DOCUMENTS

| | | |
|---|---|---|
| CN | 105208958 A | 12/2015 |
| CN | 105899143 A | 8/2016 |

(Continued)

OTHER PUBLICATIONS

German Office Action for German Patent Appplication No. 102020208325.8 dated May 3, 2021.

*Primary Examiner* — Kibrom K Gebresilassie
(74) *Attorney, Agent, or Firm* — Harness, Dickey & Pierce, P.L.C.

(57) ABSTRACT

A method is for creating a navigation plan for a catheter in tissue in dependence on a limit value distribution. In an embodiment, the method includes acquiring first elasticity data of the tissue via a first imaging modality; reading in first image data and assigning the first elasticity data to the first image data; determining the limit value distribution at least in dependence on the first elasticity data and assigning the limit value distribution to the first image data; and creating the navigation planfor the catheter in the tissue at least in dependence on the first image data and the limit value distribution.

17 Claims, 6 Drawing Sheets

(56)                    References Cited

U.S. PATENT DOCUMENTS

| | | |
|---|---|---|
| 2004/0009459 A1 | 1/2004 | Anderson et al. |
| 2004/0015070 A1 | 1/2004 | Liang et al. |
| 2005/0256398 A1 | 11/2005 | Hastings et al. |
| 2009/0105579 A1 | 4/2009 | Garibaldi |
| 2011/0093243 A1 | 4/2011 | Tawhai et al. |
| 2013/0296737 A1 | 11/2013 | Mcmillan et al. |
| 2014/0303486 A1 | 10/2014 | Baumgartner et al. |
| 2015/0351860 A1 | 12/2015 | Piron et al. |
| 2016/0302869 A1 | 10/2016 | Chopra |
| 2016/0324584 A1 | 11/2016 | Tahmasebi Maraghoosh et al. |
| 2018/0085167 A1 | 3/2018 | Goyal |
| 2018/0161099 A1 | 6/2018 | Dumenil et al. |
| 2019/0304129 A1* | 10/2019 | Schafer ................ A61B 1/2676 |
| 2020/0155243 A1 | 5/2020 | Crawford et al. |

FOREIGN PATENT DOCUMENTS

| | | |
|---|---|---|
| CN | 107847277 A | 3/2018 |
| CN | 108697469 A | 10/2018 |
| WO | WO 03086190 A1 | 10/2003 |

* cited by examiner

METHOD AND SYSTEM FOR CREATING A NAVIGATION PLAN FOR A CATHETER WITH A ROBOT

PRIORITY STATEMENT

The present application hereby claims priority under 35 U.S.C. § 119 to German patent application number DE 102020208325.8 filed Jul. 2, 2020, the entire contents of which are hereby incorporated herein by reference.

FIELD

Example embodiments of the invention generally relate to a method for creating a navigation plan for a catheter in tissue in dependence on a limit value distribution, a robot for navigating a catheter into a target region of tissue of a medical target object in dependence on a navigation plan and a system comprising a robot, a first imaging modality and/or a second imaging modality and a computing unit, which is embodied to determine a limit value distribution at least in dependence on first elasticity data and first image data and to create a navigation plan.

BACKGROUND

In many cases, it is necessary to align medical objects very precisely relative to a medical target object. Such a medical target object may, for example, be a patient or a simulator, also called a dummy, for simulating the patient. The medical object, in particular a catheter or a needle, can, for example, be introduced into the medical target object.

In particular in the case of a catheter, the medical target object should be aligned in dependence on a previously created navigation plan. A navigation plan can, for example, comprise a path or trajectory on which the medical object is aligned and/or moved. Such a navigation plan can, for example, be planned in advance based on information on the medical target object. Information of this kind can, for example, be based on image data from an imaging modality, such as, for example, an ultrasound apparatus, an X-ray apparatus, a computed tomography apparatus or a magnetic resonance apparatus, for the medical target object. In a specific example, it can be provided that the catheter is guided to a target region within the patient or the dummy. Herein, as described above, the catheter should in particular be guided along the predetermined path or the trajectory of the navigation plan.

Herein, the target region inside the patient may, for example, be a tumor, a hematoma or an aneurysm. However, precise positioning of a medical object is also necessary in many other situations.

A so-called guide unit can be used to guide or navigate the catheter. The guide unit can be configured to transmit three-dimensional movements to the catheter or needle in order to navigate the catheter or needle in the medical object. Herein, the guide unit can, for example, be connected to a dedicated robot or an imaging modality. It is in particular conceivable for the guide unit to be controlled by an operator, such as, for example, a surgeon, in order to navigate the catheter or the needle into the target region of the medical target object. Herein, an operator of the guide unit can in particular make use of real-time image data from an imaging modality and the navigation plan.

SUMMARY

While the navigation plan can be created based upon the image data with common methods, the inventors have discovered that it is not always possible to avoid complications when navigating the catheter in the medical target object. Complications constitute, for example, an injury to a vessel wall, a rupture of an aneurysm or the detachment of thrombi on a vessel wall due to the catheter. The inventors have discovered that conventional methods for creating the navigation plan cannot address these problems adequately since, inter alia, it is necessary for the operator to have extensive experience with the robot in order to estimate tissue stress.

Embodiments of the present invention provide a method, a robot, a system and a computer program product that improve navigation planning and reduce the risk of complications when navigating the catheter in the medical target object.

Advantageous embodiments and expedient developments are the subject matter of the claims.

In the method according to at least one embodiment of the invention, a navigation plan for a catheter in tissue is created in dependence on a limit value distribution comprising spatially resolved limit values for maximum force absorption and/or a permissible deflection of volume elements of the tissue.

Herein, an intervention, i.e. the actual navigation of the catheter into the target region of the medical target object, can in particular take place independently of the method according to at least one embodiment of the invention for the creation of the navigation plan with the above-described embodiments and should hence be considered separately therefrom.

The robot according to at least one embodiment of the invention for navigating the catheter into the target region of the tissue of the medical target object has a guide unit, which is embodied to change a position and/or orientation of the catheter. Herein, the robot can be electrically and/or mechanically connected to an external computing unit and the first imaging modality and/or the second imaging modality. For this purpose, the robot preferably has a dedicated interface configured to provide a signal connection for the transmission of information to the external computing unit, the first imaging modality and/or the second imaging modality. An interface can be embodied as any type of network interface, such as, for example, an RJ-45 interface, any type of bus interface, such as, for example, a CAN bus interface, or as an electrical connection for transmitting analog and/or digital signals. The robot can further be embodied as a stand-alone component. In this case, the robot can have an integrated computing unit, or also an interface for the signal connection with the first imaging modality and/or the second imaging modality.

The system according to at least one embodiment of the invention comprises a robot according to at least one embodiment of the invention, a first imaging modality and/or a second imaging modality and a computing unit with a signal connection to the robot, the first imaging modality and/or the second imaging modality and which is embodied to determine the limit value distribution at least in dependence on the first elasticity data and the first image data and to create a navigation plan according to a method according to the invention. The robot, the first imaging modality and/or the second imaging modality and the computing unit are preferably embodied according to one of the above-described embodiments. Herein, the computing unit can be mechanically connected to any system component, such as, for example, the first imaging apparatus, the second imaging apparatus, the robot or the display unit. It is likewise conceivable for the computing unit to be embodied as an independent component. The computing unit preferably has a dedicated interface configured to provide a signal connection to the robot, the first imaging modality and/or the second imaging modality. The computing unit is in particular configured to determine the limit value distribution at least in dependence on the first elasticity data and the first image data. Herein, the first elasticity data and the first image data can be transmitted to the computing unit from the first imaging modality and/or the second imaging modality via the interface or read in from a database. The computing unit's processor is preferably embodied to determine the limit value distribution via a biomechanical model or a model-based approach according to an above-described embodiment and to create the navigation plan for the catheter in the tissue at least in dependence on the first image data and the limit value distribution.

The computer program product according to at least one embodiment of the invention can be loaded directly into a memory of the computing unit of the system and has program code segments in order to execute a method according to at least one embodiment of the invention when the computer program product is executed in the computing unit of the system. The computer program product according to at least one embodiment of the invention enables the method according to at least one embodiment of the invention to be executed in a quick, identically repeatable and robust manner.

The computer program product is configured such that it can execute the method steps according to at least one embodiment of the invention via the computing unit. Herein, the computing unit must in each case fulfill the requisite conditions such as, for example, an appropriate random-access memory, an appropriate graphics card or an appropriate logic unit so that the respective method steps can be executed efficiently.

The computer program product is for example stored on a computer-readable medium or held on a network, a server or a cloud from where it can be loaded into the processor of a local computing unit, which can be embodied as an independent system component or as a part of the first imaging modality, the second imaging modality, the display unit or the robot. Furthermore, control information for the computer program product can be stored on an electronically readable data carrier. The control information of the electronically readable data carrier can be embodied such that it can carry out a method according to at least one embodiment of the invention when the data carrier is used in a computing unit of a combined imaging device. Examples of electronically readable data carriers are a DVD, a magnetic tape or a USB stick on which electronically readable control information, in particular software, is stored. When this control information is read from the data carrier and in stored in a controller and/or computing unit of a system according to at least one embodiment of the invention, all the embodiments according to the invention of the above-described methods can be carried out.

A method according to at least one embodiment of the invention is for creating a navigation plan for a catheter in tissue in dependence on a limit value distribution including spatially resolved limit values for at least one of maximum force absorption and a permissible deflection of volume elements of the tissue, the method comprising:

acquiring first elasticity data of the tissue via a first imaging modality, the first elasticity data including spatially resolved elasticity values of volume elements of the tissue;

reading in first image data and assigning the first elasticity data to the first image data, an elasticity value of a volume element of the tissue being allocated to a volume element of the tissue of the first image data;

determining the limit value distribution at least in dependence on the first elasticity data and assigning the limit value distribution to the first image data, a limit value of a volume element of the tissue being allocated to a volume element of the tissue of the first image data; and creating the navigation plan for the catheter in the tissue at least in dependence on the first image data and the limit value distribution.

A robot according to at least one embodiment of the invention is for navigating a catheter into a target region of tissue of a medical target object, the robot comprising:

a guide unit, embodied to change at least one of a position and an orientation of the catheter, and the catheter being controllable via the guide unit in dependence on a navigation plan including:

acquiring first elasticity data of the tissue via a first imaging modality, the first elasticity data including spatially resolved elasticity values of volume elements of the tissue;

reading in first image data and assigning the first elasticity data to the first image data, an elasticity value of a volume element of the tissue being allocated to a volume element of the tissue of the first image data;

determining the limit value distribution at least in dependence on the first elasticity data and assigning the limit value distribution to the first image data, a limit value of a volume element of the tissue being allocated to a volume element of the tissue of the first image data; and creating the navigation plan for the catheter in the tissue at least in dependence on the first image data and the limit value distribution.

BRIEF DESCRIPTION OF THE DRAWINGS

Further advantages and details of the present invention can be derived from the example embodiments described below and with reference to the drawings, in which.

DETAILED DESCRIPTION OF THE EXAMPLE EMBODIMENTS

Figure 1:
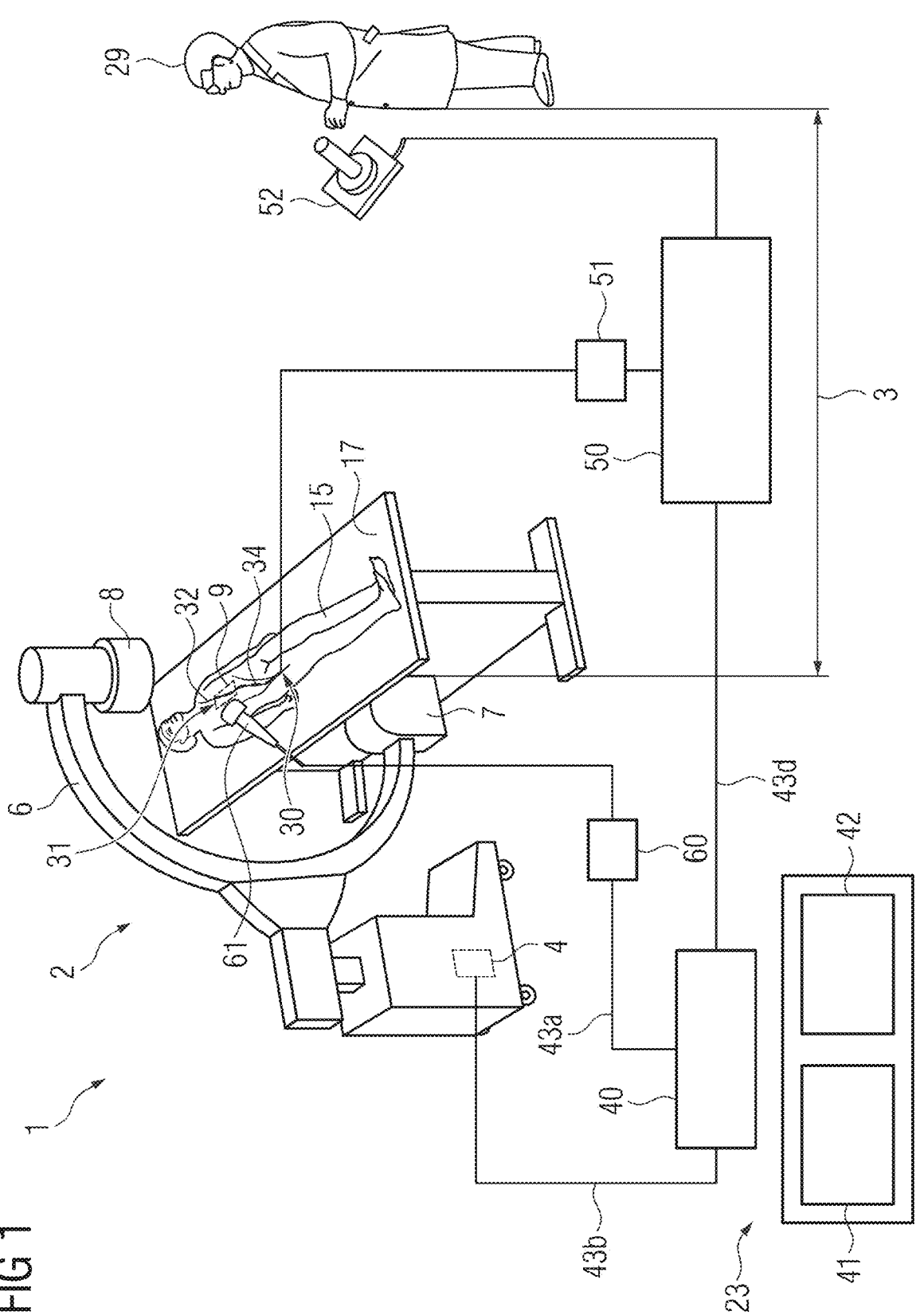
FIG. 1 shows an embodiment of a system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the method according to at least one embodiment of the invention, a navigation plan for a catheter in tissue is created in dependence on a limit value distribution comprising spatially resolved limit values for maximum force absorption and/or a permissible deflection of volume elements of the tissue.

Herein, a navigation plan of at least one embodiment can comprise multidimensional information on the tissue (tissue information) of a medical target object and a positioning instruction for the catheter. Tissue can, for example, comprise a section of skin, an organ, a vessel or any body region of a patient. Tissue information constitutes, for example, contrast, elasticity value, maximum force absorption, permissible deflection, density, tissue type, risk factor for rupture or any other indication that determines a property of the tissue and/or may be relevant for the navigation of the catheter in the tissue. A positioning instruction can, for example, comprise a direction vector or a sequence of direction vectors describing a path of the catheter through the tissue, such as, for example, a vascular tree of a patient. It is likewise conceivable for the positioning instruction to have a plurality of two-dimensional or three-dimensional coordinates which can be transmitted to a guide unit in order to guide the catheter. Herein, the navigation plan preferably comprises spatially resolved tissue information. This spatially resolved tissue information can, for example, constitute contrasts of a magnetic resonance measurement, computed tomography measurement, ultrasound measurement and/or X-ray measurement that spatially resolve anatomical structures of the tissue. The spatially resolved contrasts are preferably linked to further tissue information, such as, for example, maximum force absorption and/or a permissible deflection of a volume element of the tissue. This enables a multidimensional virtual image of the tissue to be obtained, which is, for example, present as a plurality of vectors, a matrix or a plurality of tuples. Maximum force absorption preferably constitutes the amount of a force that can be exerted onto a volume element of tissue without damaging the tissue. A permissible deflection of a volume element of the tissue can constitute elastic displacement of the tissue after which the tissue can return to its original position without damage. Herein, the tissue can in particular constitute a vessel or a vessel wall, but also an organ.

In one step of the method of at least one embodiment, first elasticity data of the tissue is acquired via a first imaging modality, wherein the first elasticity data comprises spatially resolved elasticity values of volume elements of the tissue. An imaging modality can constitute a medical device suitable for performing an imaging method for acquiring image data and/or for recording any spatially resolved measured values of tissue. A first imaging modality can, for example, be a magnetic resonance apparatus, an ultrasound apparatus or a 3D ultrasound apparatus. It is conceivable that, although the first elasticity data is recorded via an imaging modality, the creation of image data of an anatomical structure is avoided during the acquisition of the first elasticity data. The first imaging modality is in particular configured to perform an elastography measurement in which elasticity data of the tissue is acquired. Here, excitation of the tissue can take place, for example via a sound wave, pressure wave, and/or static or cyclic compression which causes compaction, displacement and/or time-dependent vibration in the tissue. Likewise, targeted tactile palpation or measurement of vascular and tissue deformation caused by a catheter, robotic catheter and/or another measuring instrument can constitute a possible method for determining elasticity values. Herein, tissue regions with different elastic properties can react differently to the excitation and can be differentiated when the first elasticity data are acquired.

The first elasticity data comprises spatially resolved elasticity values of volume elements of the tissue. This can mean that a measured elasticity value, for example in the form of a tuple, vector or matrix, is linked to a coordinate or position information in the tissue. Possible measuring methods constitute, for example, magnetic resonance elastography, ultrasound-based shear wave elastography and compression elastography. The first elasticity data preferably comprises elasticity values of a section of a vessel that includes a path of the catheter through the vessel from a starting point to a target region. Herein, a starting point can constitute an opening on an artery or vein of a medical examination object. A target region can, for example, be a hematoma, tumor, aneurysm or the like in a vessel or an organ close to a vessel.

In a further step of the method according to at least one embodiment of the invention, first image data is read in and the first elasticity data is assigned to the first image data, wherein an elasticity value of a volume element of the tissue is allocated to a volume element of the tissue of the first image data. First image data can have spatially resolved contrasts of anatomical structures in the tissue of the medical target object. Herein, a contrast can, for example, constitute a gray-scale value of a volume element which encodes spatially resolved tissue information, such as, for example, the density or proton content of the volume element. It is conceivable for the first elasticity data and the first image data to be based on a common coordinate system so that an elasticity value of a volume element can be assigned to a corresponding contrast of a volume element based on coordinates. It is likewise conceivable for the first image data to be assigned to the first elasticity data via an image registration method. Examples of image registration methods are area-based and feature-based methods, for example based on correlation, pattern recognition, a (Fourier) transform, correspondence of control points, and methods based on rigid or elastic models.

During the assignment, the elasticity values and the gray-scale values of the volume elements can, for example, be stored as a tuple, vector or matrix. It is likewise conceivable for the elasticity values and the gray-scale values of the volume elements to be present separately from one another and allocated via common indices or identifiers. Herein, a spatial resolution of the first elasticity data can differ from a spatial resolution of the first image data. It is hence conceivable for the first image data to have a higher spatial resolution so that an elasticity value of the first elasticity data is assigned to a plurality of volume elements of the first image data. However, it is likewise conceivable for the first elasticity data to have a higher spatial resolution than the first image data or for the spatial resolution of the first elasticity data to match the resolution of the first image data.

The first image data preferably comprises spatially resolved contrasts of anatomical structures in the tissue of the medical target object. Herein, the first image data in particular comprises contrasts of a section of the tissue that includes a path of the catheter through the vessel from a starting point to a target region.

Reading in first image data can mean that the first image data is obtained from a database, a local memory, cloud storage, a server and/or a control unit of an imaging modality. Herein, it is conceivable for the first image data also to comprise patient information. Such patient information can comprise demographic data, such as, for example, age, height, weight or gender, and treatment data, such as, for example, treatment history, medical history and/or information on known intolerances. It is further conceivable for the target region and/or another anatomical structure relevant for the creation of the navigation plan to be already contrasted in the first image data.

In a further step of the method according to at least one embodiment of the invention, the limit value distribution is determined at least in dependence on the first elasticity data and assigned to the first image data, wherein a limit value of a volume element of the tissue is allocated to a volume element of the tissue of the first image data. The limit value distribution comprises spatially resolved limit values for maximum force absorption and/or permissible deflection of volume elements of the tissue. It is conceivable for the limit value distribution to be determined based on the first elasticity data. In this case, the spatially resolved limit values of the limit value distribution can be assigned to the coordinates and/or the position information of the first elasticity data. It is likewise conceivable for the limit value distribution to be determined in dependence on tissue information of the first elasticity data and the first image data. Herein, the coordinates and/or the position information of the spatially resolved limit values can result from the assignment of the first elasticity values to the contrasts of the first image data. Accordingly, the limit value distribution can be present in the form of tuples, vectors or a matrix, wherein each limit value of a volume element is assigned to a coordinate and/or position information in the medical target object. It is further conceivable that the limit value of a volume element can be assigned to a corresponding elasticity value of the first elasticity data and/or a corresponding gray-scale value of the first image data via an index or identifier.

Herein, the spatial resolution of the limit value distribution can match the spatial resolution of the first elasticity data and/or the second elasticity data. In particular, the spatial resolution of the limit value distribution can match the lower spatial resolution of the first image data or the first elasticity data.

The determination of the maximum force absorption and/or the permissible deflection of the tissue can, for example, take place in dependence on tissue-typical fatigue characteristics or tissue-typical parameters. Such fatigue characteristics or parameters can, for example, indicate an area-related application of force above which rupture of the tissue is probable. The limit values of the volume elements of the tissue are preferably determined such that a safety distance to the maximum force absorption and/or permissible deflection is taken into account.

In one step of the method according to at least one embodiment of the invention, the navigation plan for the catheter in the tissue is created at least in dependence on the first image data and the limit value distribution. As described above, the navigation plan can comprise multidimensional tissue information on the medical target object and/or positioning instructions for the catheter in the tissue. The creation of the navigation plan can, for example, comprise the creation of a matrix, which at least has the limit values and the contrasts of the tissue in dependence on the coordinates and/or position information of the respective volume elements. For this purpose, the limit values and the contrasts can, for example, be stored as vectors and assigned to a corresponding vector with coordinates and/or position information on the volume elements. However, it is likewise conceivable for the limit values and contrasts to be allocated to the coordinates and/or position information in the form of tuples. Further, the first image data and the limit value distribution can be present in the form of a k-space matrix and transformed via a transform, such as, for example, a Fourier transform, into a three-dimensional image of the tissue.

The creation of a positioning instruction for the catheter can, for example, comprise taking into account direction-dependent information on the maximum force absorption and/or the permissible deflection of a volume element of the tissue. In one example, at least one elasticity value and type, position, orientation and/or material composition of a volume element of the tissue can be used in order to predict a reaction of the tissue when force is applied via a catheter. The volume element of the tissue is preferably a section of a vessel wall which is deformed by contact with the catheter. The deformation of the vessel wall can, for example, be determined based on the elasticity values of the vessel wall and the volume elements of the adjacent tissue and an assumed or predetermined direction of force application by the catheter. It is conceivable for the creation of the navigation plan to comprise the creation of a path of the catheter through the vessel or a vascular tree that avoids exceeding the maximum force absorption and/or the permissible deflection along the path through the vascular tree. Depending on the path, it is possible to derive a positioning instruction, which can, for example, be transmitted to a computing unit or a guide unit of a robot. The positioning instruction can, for example, comprise a sequence of coordinates and/or direction vectors which are converted into a movement of the catheter via the guide unit.

It is further conceivable for the maximum force absorption and/or the permissible deflection of the vessel wall along the path of the vessel or vascular tree to be output together with the first image data via the navigation plan and transmitted to a display unit. Herein, the maximum force absorption and/or the permissible deflection of the vessel wall can be converted via a function into color values which can be displayed on the display unit.

The creation of a navigation plan in dependence on the limit value distribution advantageously makes it possible to reduce the risk of complications when navigating the catheter into the target region of a medical target object.

In one possible embodiment of the method according to the invention, first image data of the tissue is acquired via the first imaging modality and/or a second imaging modality. A second imaging modality can, for example, constitute a magnetic resonance apparatus, a computed tomography apparatus, an ultrasound apparatus, an X-ray apparatus or the like. Herein, the second imaging modality can constitute an imaging modality different from the first imaging modality. In one example, the first imaging modality can be a magnetic resonance apparatus, while the second imaging modality is an ultrasound apparatus. During the acquisition of the first image data, it is conceivable for spatially resolved contrasts of anatomical structures in the tissue of the medical target object to be recorded and stored in a database. It is furthermore conceivable for the acquisition of the first image data to precede the acquisition of first elasticity data in terms of time or to take place in parallel thereto. Precedence in terms of time can mean that the acquisition of the first image data takes place several weeks, several days, several hours or a few minutes before the acquisition of the first elasticity data. Parallel acquisition of the first image data and the first elasticity data can mean that a period of acquisition of the first elasticity data at least partially overlaps a period of acquisition of the first image data in terms of time. The first image data is preferably recorded immediately before the acquisition of the first elasticity data or the determination of the limit value distribution, wherein the medical target object remains in a predetermined position relative to the first imaging modality and/or the second imaging modality.

The timely acquisition of the first image data and the first elasticity data advantageously enables a relative position between the medical target object and the first imaging modality and/or the second imaging modality to be kept constant during the creation of the navigation plan. This advantageously enables the assignment of the contrasts of the first image data and the elasticity values of the first elasticity data to be simplified. In addition, the timely acquisition of the first image data and the creation of the navigation plan enables a current state of the medical target object to be acquired, thus enabling the risk of complications due to unexpected pathological structures along the planned path to be reduced.

In a further embodiment of the method according to the invention, a parameter set of the first imaging modality and/or the second imaging modality is selected during the acquisition of first image data such that a deposit in a vessel of the tissue is detected, wherein the creation of the navigation plan takes place in dependence on information on the deposit in the vessel. A parameter set can, for example, comprise a plurality of imaging parameters of the first imaging modality and/or the second imaging modality with which a contrast, a resolution, an imaging region, a recording duration or the like can be adjusted. Examples of such imaging parameters of a magnetic resonance apparatus are: a $T1$ and/or $T2$ relaxation time, a slice thickness, a speed of movement of the medical target object relative to the magnetic resonance apparatus, an imaging sequence or the like. On the other hand, imaging parameters of an X-ray apparatus can comprise a radiation dose, a voltage and/or a current of an X-ray tube, a quality of a radiation focus and a use and quality of an X-ray filter, a distance between the medical target object and an X-ray source or the like. In addition to the aforementioned imaging modalities, it is also possible to use further imaging modalities, such as, for example, computed tomography apparatuses or ultrasound apparatuses and/or further imaging parameters known to the person skilled in the art.

A deposit can, for example, constitute a thrombus, atherosclerotic plaque or the like. The deposit can, for example, be positioned on an inner surface of the vessel wall and differ in composition from the surrounding tissue. The composition of the deposit preferably differs from the surrounding tissue in such a way that a contrast of a volume element of the deposit in the first image data can be adjusted by adapting the parameter set of the first imaging modality and/or the second imaging modality. The atherosclerotic plaque can, for example, have a high content of calcium phosphate. Accordingly, the contrast of the atherosclerotic plaque can be increased by adjusting the parameter set which takes account of the high calcium phosphate content. In the example of a magnetic resonance measurement, a plurality of differently weighted imaging sequences can be used to increase (for example via a gradient echo sequence) or reduce (for example via a spin echo sequence) the signal intensity of the blood compared to the deposit. The use of computed tomography angiography and/or color-coded Doppler sonography with corresponding parameter sets which are known to the person skilled in the art is likewise conceivable. It is further conceivable that, before the acquisition of the first image data, the medical target object is given a contrast agent which increases the contrast of the deposit, the blood or the tissue surrounding the deposit in the first image data. The deposit is preferably registered in the navigation plan. This can mean that, depending upon their position information and/or coordinates, contrasts of the deposit are superimposed or merged with corresponding contrasts of the first image data of the navigation plan.

The detection of deposits in the vascular tree by adapting the parameter set of the first imaging modality and/or the second imaging modality enables information on a pathological state of the medical target object relevant for navigation of the catheter to be advantageously output with the navigation plan and/or taken into account during the creation of the navigation plan. Depending on the output of the deposit, the path of the catheter in the vessel can advantageously be adapted and the risk of stroke as the result of the detachment of a deposit due to contact with the catheter reduced.

According to a further embodiment of the method according to the invention, a parameter set of the first imaging modality and/or the second imaging modality is selected during the acquisition of the first image data such that an accumulation of fluid in the tissue is localized, wherein the creation of the navigation plan takes place in dependence on information on the accumulation of fluid in the tissue. An accumulation of fluid can, for example, constitute a vascular aneurysm or a hematoma on a vessel wall. As described above, the parameter set of the first imaging modality and/or the second imaging modality can be adapted in order to detect an increased contrast of an accumulation of fluid in the tissue of the medical target object. Herein, the tissue can in particular constitute a vascular tree. In one example, the first imaging modality is a magnetic resonance apparatus in which the parameter set can comprise a T1 weighted spin echo sequence with fat saturation in order to obtain an increased contrast of the hematoma in the first image data.

It is conceivable for contiguous volume elements of the first image data with high contrasts or contrasts above a predetermined threshold to be identified as an accumulation of fluid and registered with the navigation plan. It is further conceivable for the accumulation of fluid to constitute the target region of the catheter in the tissue of the medical target object. In this case, the path of the catheter through the vessel or the vascular tree and/or the positioning instruction for the navigation plan can be adapted such that the catheter can be guided to the accumulation of fluid in the medical target object. In a further example, the detected accumulation of fluid constitutes an aneurysm which is associated with an increased risk of complications. If there is an imminent risk of rupture of the aneurysm, the path of the catheter through the vessel or the vascular tree and/or the positioning instruction for the navigation plan can be adapted such that direct contact of the catheter with the aneurysm is avoided. It is for example conceivable for the catheter to be guided along an alternative section of the vascular tree during navigation into the target region in order to avoid contact with the accumulation of fluid. Herein, the risk of vascular rupture can, for example, be ascertained via biomechanical models or model-based approaches.

The adaptation of the parameter set of the first imaging modality and/or the second imaging modality to detect accumulations of fluid in the vascular tree enables information on a pathological state of the medical target object relevant for navigation of the catheter to be advantageously output together with the first image data and/or the navigation planning. Depending on the spatial position of the accumulation of fluid, the path of the catheter in the vascular tree of the tissue can be planned more efficiently during the creation of the navigation plan, thus advantageously enabling the duration of the navigation of the catheter into the target region to be reduced. Further, accumulations of fluid, which entail an increased risk of complications upon contact with the catheter, can be taken into account during the creation of the navigation plan, thus advantageously enabling the risk of vascular rupture to be reduced.

In one possible embodiment of the method according to the invention, second image data of the tissue is acquired via the first imaging modality or the second imaging modality, wherein a parameter set of the first imaging modality or the second imaging modality during the acquisition of the second image data is selected such that a travel speed of a fluid in the vessel of the tissue is determined, wherein the creation of the navigation plan takes place in dependence on information on the travel speed of the fluid in the vessel of the tissue. It is conceivable for the second image data to comprise spatially resolved speed values and/or speed vectors of the blood in the tissue of the medical target object. Herein, the second image data and the first image data and/or the first elasticity data can be based on a common coordinate system so that a speed value and/or a speed vector can be assigned to a corresponding contrast and/or an elasticity value of a volume element during the creation of the navigation plan based on coordinates. As described above, the second image data, the first image data and/or the second elasticity data can also be transformed or reshaped in order to enable the assignment. Herein, the acquisition of the second image data preferably precedes the creation of the navigation plan in terms of time. Herein, the second image data can be recorded in parallel to the acquisition of the first image data or the first elasticity data.

It is conceivable for the speed values and/or speed vectors of the second image data to be used to ascertain hemorrhaging, vasoconstriction and/or vasodilation. Changes to the cross section of the vessel can cause local changes to the flow rate in the vessel thereby identifying deposits or aneurysms. Information on a local change to the flow rate is preferably registered as a potential deposit or a potential aneurysm in the navigation plan. For the detection of local changes to the flow rate, it is, for example, possible to determine mean values of the flow rate at discrete intervals along the blood vessel. The information on local changes to the flow rate is preferably taken into account when planning the path of the catheter in the vessel of the medical examination object.

The determination of the flow rate of the blood in the vascular tree can enable information on a local constriction and/or a dilation of the cross section of the vessel, and also hemorrhaging, to be obtained. The information on a local constriction and/or dilation of the cross section of the vessel can advantageously be combined with information on an accumulation of fluid and/or a deposit from the first image data in order to improve an evaluation of the risk of complications for the medical target object.

In a further embodiment of the method according to the invention, the limit value distribution is determined via a biomechanical model of the tissue and/or a model-based approach. A biomechanical model of the tissue can comprise an artificial and/or virtual replica of the tissue with the aid of mechanical, anatomical and/or physiological laws. In particular, the biomechanical model can be suitable for determining and/or predicting a property and/or behavior of the tissue, such as, for example, an elasticity value or deformation, under dynamic conditions, such as, for example, movement of the medical target object or the application of force by the catheter. It is conceivable for the biomechanical model to be able to read in spatially resolved tissue information from the first image data, the second image data and/or the first elasticity data in order to determine the properties and/or the behavior of the tissue. The biomechanical model is in particular configured to determine deformation of a vessel caused by the guidance of the catheter along the vessel. For this purpose, the biomechanical model can inter alia comprise information on a material parameter and/or a structural design of the catheter, which is used to determine deformation and/or the application of force on the vessel wall by the catheter. It is conceivable for a maximum application of force and/or a permissible deflection of volume elements of the tissue to be determined via the biomechanical model and stored or output as a limit value distribution. Herein, the biomechanical model preferably comprises a subdivision of the tissue into a finite number of sub-bodies and equation systems, boundary conditions and numerical methods for determining the properties and/or the behavior of the sub-bodies of the tissue.

In this context, a model-based approach can, for example, comprise a model, an algorithm or a function with which a property and/or behavior of the tissue can be determined in a simplifying manner in dependence on predetermined input variables. Herein, an input variable can constitute any tissue information from the first image data, the second image data, the first elasticity data and also patient information. Preferably, subdivision of the tissue into a number of sub-bodies is avoided when the model-based approach is used. It is, for example, conceivable for the model-based approach to have a fitting function that determines maximum force absorption and/or a permissible deflection of the tissue in dependence on the first elasticity data and age, weight and/or a pre-existing condition (for example diabetes) of the medical target object. For this purpose, it is also possible to use statistical data, such as, for example, fragility of the vessels in dependence on age, weight or a pre-existing condition.

It is likewise conceivable for the model-based approach to determine a contour of the vessel or the vessel wall as a result of the application of force by the catheter. Here, it is possible to adapt coefficients, such as, for example, polynomial coefficients, spline coefficients or the like, describing the course of the application of force by the catheter on the vessel wall and/or resulting deformation of the contour the vessel wall in dependence on the first elasticity values and the application of force in a simplifying manner via an interpolation function, a regression method or fitting calculation (curve fitting). This method enables any kind of spatially resolved information on deformation and/or elasticity of the tissue and the vessel wall to be determined.

The use of a biomechanical model or a model-based approach advantageously enables the determination of limit values for maximum force absorption and/or the permissible deflection of the tissue to be determined in dependence on individual items of information on the medical target object, such as, for example, the tissue information from the first image data, the second image data, the first elasticity data and/or the patient information. As a result, the navigation plan can be adapted to individual requirements of a medical target object and/or the risk of complications along the planned path can be predicted more efficiently.

In one possible embodiment of the method according to the invention, the navigation plan for the catheter is output. It is conceivable for the output of the navigation plan to comprise the transmission of digital and/or analog signals. The digital and/or analog signals can, for example, be transmitted to a robot, which is configured to implement a positioning instruction for the navigation plan via a guide unit. However, it is likewise conceivable for the navigation plan to be transmitted to a display unit for visualization. Herein, the display unit can constitute any device embodied to display the tissue information of the navigation plan. In one example, an anatomical structure of the medical target object can be depicted on the display unit via the contrasts of the first image data. Herein, the contrasts can be superimposed with color values indicating a limit value, an elasticity value and a planned path and/or a direction vector with a positioning instruction for the catheter. It is further conceivable for the positioning instruction for the catheter to be registered with real-time image data for the medical target object so that an operator can track the navigation plan in relation to the real-time image data for the catheter in the medical target object. Outputting of the navigation plan can further mean that the navigation plan is transmitted via a network, in particular an IP-based network or a bus system, to an imaging modality, a robot, a server and/or a computing unit.

Outputting the navigation plan advantageously enables the navigation plan to be made available to an operator for planning an intervention. Furthermore, the registration of the navigation plan with real-time image data advantageously enables a current position of the catheter in relation to a planned position of the catheter based on the navigation plan to be determined during navigation of the catheter into the target region. The navigation plan can further be output to a robot, which is embodied to restrict a movement of the catheter in dependence on the navigation plan. This can advantageously avoid any risk of injury to the vessel by the catheter.

Herein, an intervention, i.e. the actual navigation of the catheter into the target region of the medical target object, can in particular take place independently of the method according to at least one embodiment of the invention for the creation of the navigation plan with the above-described embodiments and should hence be considered separately therefrom.

The robot according to at least one embodiment of the invention for navigating the catheter into the target region of the tissue of the medical target object has a guide unit, which is embodied to change a position and/or orientation of the catheter. Herein, the robot can be electrically and/or mechanically connected to an external computing unit and the first imaging modality and/or the second imaging modality. For this purpose, the robot preferably has a dedicated interface configured to provide a signal connection for the transmission of information to the external computing unit, the first imaging modality and/or the second imaging modality. An interface can be embodied as any type of network interface, such as, for example, an RJ-45 interface, any type of bus interface, such as, for example, a CAN bus interface, or as an electrical connection for transmitting analog and/or digital signals. The robot can further be embodied as a stand-alone component. In this case, the robot can have an integrated computing unit, or also an interface for the signal connection with the first imaging modality and/or the second imaging modality.

A guide unit preferably constitutes an electrical drive, a hydraulic drive, a pneumatic drive or the like configured to transmit a movement to the catheter. Such a movement can comprise different degrees of freedom, such as, for example, a translational degree of freedom and/or a rotational degree of freedom. It is furthermore conceivable that at least a section of the catheter can be bent via the guide unit. Hence, a change in position and/or orientation of the catheter can, for example, comprise a translational movement along a trajectory of the vessel, a rotational movement of the catheter about an axis of the catheter and/or bending of the catheter.

The catheter can be controlled via the guide unit in dependence on the navigation plan. This can mean that the multidimensional tissue information and/or the positioning instruction for the navigation plan is displayed to the operator of the robot via a display unit. Hence, the operator of the robot is able to actuate the robot's guide unit and implement the positioning instruction for the navigation plan via a remote control, such as, for example, a controller, a joystick, a keyboard or the like.

It is likewise conceivable for the robot to be configured to interpret the navigation plan and/or the positioning instruction for the navigation plan via the computing unit and to move the catheter via the guide unit in dependence on release by the operator. Release by the operator can, for example, comprise continuous or discontinuous actuation of a remote-control button, which releases the movement of the catheter by the robot. The robot's computing unit is preferably configured to process a digital and/or analog signal with tissue information in the navigation plan and to actuate the guide unit accordingly.

It is furthermore conceivable for a structure, a material composition and/or a degree of freedom of the catheter to be already taken into account during the creation of the navigation plan in order to coordinate the navigation plan with the individual requirements of the robot, the catheter and/or the guide unit.

The robot can further have means for determining the tissue's force absorption. Such means can, for example, be a sensor configured to measure force absorption. Conceivable embodiments of the sensor constitute, for example, strain gauges, piezo force transducers, electrodynamic force transducers or the like. The sensor can be positioned at the tip of the catheter and connected to the robot's computing unit via an electrical signal connection along the catheter in order to transmit a measured value of the force absorption at the tip of the catheter to the computing unit. However, it is likewise conceivable for the sensor to be positioned on the guide unit and to measure force absorption of the catheter by the drive.

The computing unit is preferably embodied to determine a difference between the measured force absorption of the sensor and the maximum force absorption of the vessel wall based on the navigation plan. If a limit value is exceeded, it is, for example, possible for the intervention to be interrupted or the orientation and/or the position of the catheter to be adapted. It is likewise conceivable for the operator of the robot to be informed via a display unit when a limit value is exceeded and prompted to take action. Furthermore, the robot can be embodied to restrict the movement of the catheter in a direction that causes the one limit value to be exceeded.

Controlling the catheter in dependence on the navigation plan via the robot enables the precision of the navigation of the catheter in the tissue of the medical target object to be increased compared to manual movement of the catheter and the undesired exceeding of a limit value to be avoided.

In one possible embodiment of the robot according to the invention, the robot is configured to navigate the catheter into the target region in dependence on the navigation plan. Automatic navigation of the catheter into the target region can mean that the robot moves the catheter independently through the tissue and/or the vascular tree along a path specified by the navigation plan. The catheter has preferably already been inserted into the medical target object when navigation begins. In this embodiment, the robot preferably has a computing unit, such as, for example, a processor or microprocessor, for processing analog and/or digital information and a control unit, such as, for example, a controller or microcontroller, for conditioning and outputting control signals. The robot's computing unit is preferably embodied to transmit the positioning instruction and/or the sequence of direction vectors of the navigation plan to the guide unit via the control signals so that the catheter is navigated into the target region according to the navigation plan. Herein, the robot and/or the guide unit are in particular coordinated with the navigation plan. This can mean that the positioning instruction for the navigation plan can be implemented via the robot's guide unit and the available degrees of freedom.

Herein, the computing unit preferably determines the progress of the catheter in the tissue or the vessel, for example in that the actuation of the guide unit is correlated with a speed of movement of the catheter in the tissue in terms of time.

The use of a robot which is configured to navigate the catheter into the target region automatically in dependence on the navigation plan advantageously enables operator errors with the robot to be avoided when navigating the catheter in the tissue.

The system according to at least one embodiment of the invention comprises a robot according to at least one embodiment of the invention, a first imaging modality and/or a second imaging modality and a computing unit with a signal connection to the robot, the first imaging modality and/or the second imaging modality and which is embodied to determine the limit value distribution at least in dependence on the first elasticity data and the first image data and to create a navigation plan according to a method according to the invention. The robot, the first imaging modality and/or the second imaging modality and the computing unit are preferably embodied according to one of the above-described embodiments. Herein, the computing unit can be mechanically connected to any system component, such as, for example, the first imaging apparatus, the second imaging apparatus, the robot or the display unit. It is likewise conceivable for the computing unit to be embodied as an independent component. The computing unit preferably has a dedicated interface configured to provide a signal connection to the robot, the first imaging modality and/or the second imaging modality. The computing unit is in particular configured to determine the limit value distribution at least in dependence on the first elasticity data and the first image data. Herein, the first elasticity data and the first image data can be transmitted to the computing unit from the first imaging modality and/or the second imaging modality via the interface or read in from a database. The computing unit's processor is preferably embodied to determine the limit value distribution via a biomechanical model or a model-based approach according to an above-described embodiment and to create the navigation plan for the catheter in the tissue at least in dependence on the first image data and the limit value distribution.

The system according to at least one embodiment of the invention enables a system structure and/or a relative position of the system components to be spatially defined. This enables the provision of a common coordinate system for the first imaging modality and the second imaging modality, which advantageously simplifies the assignment and/or registration of the first image data with the first elasticity data. The system structure further enables optimization of a communication infrastructure and/or an exchange of information between the system components and the computing unit. This advantageously enables the time required for the transmission and processing of information to be reduced.

In a further embodiment of the system according to the invention, the first imaging modality and/or the second imaging modality is embodied to acquire second elasticity data during navigation of the catheter into the target region, wherein the computing unit is embodied to update the limit value distribution and the navigation plan in dependence on the second elasticity data. Herein, the second elasticity data is preferably recorded with an imaging facility with which the first elasticity data is also recorded. The acquisition of the second elasticity data can take place according to one of the above-described embodiments. The first imaging facility and/or the second imaging facility is preferably embodied to store spatially resolved elasticity values of second elasticity data together with corresponding coordinates and/or position information in the form of tuples, vectors or a matrix and/or to transmit them to the computing unit via a signal connection. The computing unit can be embodied to complement, update and/or overwrite the limit value distribution and the navigation plan based on the second elasticity data and the first image data. For this purpose, the computing unit preferably has a synchronization component which ensures database consistence when elasticity values are acquired and changed in parallel. However, it is likewise conceivable for the computing unit to be embodied to determine a second limit value distribution at least in dependence on the second elasticity data. In this case, the creation of the navigation plan can take place accordingly by weighting the first limit value distribution and the second limit value distribution.

The acquisition of second elasticity data during navigation of the catheter into the target region enables an influence of the catheter on the elasticity values of the vessel in the vicinity of the catheter to be determined by metrological means. This enables the limit value distribution determined in dependence on models to be complemented with measurement data and the accuracy of the determination of the maximum force absorption and/or the permissible deflection of the tissue to be advantageously increased.

In a further embodiment of the system according to the invention, the robot comprises a sensor with a signal connection to the computing unit and which is configured to acquire the force absorption of a volume element of the tissue during navigation of the catheter into the target region. Herein, a sensor can be embodied according to one of the above-described embodiments. The sensor preferably has a direct or indirect signal connection to the computing unit in order to transmit the measured values of the force absorption. Herein, a direct signal connection can constitute an electrical connection for the transmission of analog or digital information. An indirect signal connection can mean that the information transmitted by the sensor is processed and/or conditioned, i.e. converted into any data format, by a further processor, which is, for example, positioned on the sensor or robot, before transmission to the computing unit.

The computing unit is configured to output information and/or limit movement of the catheter when the limit value of the force absorption of a volume element of the tissue is exceeded. The information can, for example, constitute a positioning instruction for the navigation plan. Herein, the positioning instruction can comprise a limitation of the movement of the catheter which causes impermissible deflection and/or exceeding of the maximum force absorption of the tissue. The positioning instruction can in particular also comprise a signal for terminating movement of the catheter.

It is furthermore conceivable for the information to comprise an indication or warning. Herein, the display unit can be configured to output the indication or warning in order, for example, to inform the operator that a limit value has been exceeded or that exceeding of a limit value due to the movement of the catheter is imminent. It is further conceivable for a property of the indication to be adapted in dependence on the measured force absorption. Herein, the indication can comprise any object whose color, shape, positioning and/or geometry can be changed in dependence on the measured force absorption of the tissue.

The measurement of the force absorption via the sensor advantageously enables movement of the catheter to be automatically limited in the event of a maximum force absorption of the tissue being exceeded. This advantageously enables the reduction of damage to the tissue, for example as a result of unintentional contact with a vessel wall.

In a further embodiment of the system according to the invention, the first imaging modality and/or the second imaging modality is embodied to acquire third image data during navigation of the catheter into the target region. Similarly to the first image data, third image data can have spatially resolved contrasts of anatomical structures in the medical target object. The third image data preferably also contains spatially resolved contrasts of the catheter or parts of the catheter. Herein, an imaging region of the first imaging modality and/or the second imaging modality can in particular be directed at or adapted to the catheter and tissue surrounding the catheter.

In this embodiment, the computing unit is configured to determine force absorption and/or a deflection of a volume element of the tissue in dependence on the third image data and to output information if the limit value of the maximum force absorption and/or the permissible deflection of a volume element of the tissue is exceeded. It is conceivable for the computing unit to have an image processing unit embodied to quantify a difference between a spatial position of a volume element of the tissue of the third image data from the spatial position of the volume element of the tissue of the first image data. This difference can constitute a deflection that takes place as a result of the navigation of the catheter in the tissue. Herein, the first image data can, for example, be used as a reference measurement. The computing unit is preferably further embodied to quantify the amount by which the limit value of the deflection of the volume element is exceeded in dependence on the difference of the spatial position of the volume element of the tissue and to output this via the display unit.

The computing unit can furthermore be configured to determine force absorption of the tissue in dependence on the spatially resolved contrasts of the catheter. For this purpose, information on the catheter, such as, for example, a structural design, a material composition or a model of the catheter, can be stored in a database or a memory and read in by the computing unit. The computing unit's image processing unit can be embodied to determine deformation of the catheter, such as, for example, bending, twisting, winding or the like, in dependence on the third image data and to determine the force absorption of the tissue surrounding the catheter based on the information on the catheter. As described above, the computing unit can likewise be configured to determine whether the limit value of the force absorption of the volume element is exceeded in dependence on the deformation of the catheter. The information on whether a limit value is exceeded can be output on the display unit and/or comprise a positioning instruction which is transmitted to the robot and/or the guide unit. It is conceivable for the computing unit to update the navigation plan, in particular the positioning instruction for the navigation plan, in dependence on the third image data. Furthermore, the computing unit can be embodied to transmit the third image data together with the navigation plan to the display unit in order to inform the operator of the robot about the current position of the catheter and/or the progress of the catheter in the tissue. Herein, it is in particular conceivable for the third image data to be recorded via an X-ray apparatus or a fluoroscopy apparatus.

The acquisition of third image data advantageously enables the force absorption and/or the deflection of the tissue as a result of the movement of the catheter to be monitored and output in real-time. This can advantageously enable a risk of complications, for example due to an undesired deflection of a vessel wall, to be avoided.

In one possible embodiment of the system according to the invention, the computing unit is configured to output information on force absorption and/or a deflection of a volume element of the tissue during navigation of the catheter into the target region. Herein, the force absorption and/or the deflection of the volume element of the tissue can be measured and/or determined according to one of the above-described embodiments and updated continuously or at discrete time intervals during navigation of the catheter into the target region. Information on force absorption and/or a deflection of a volume element of the tissue can, for example, be the force absorption and/or deflection of the volume element determined based on the sensor and/or the third image data. However, it is likewise conceivable for the information to be determined in dependence on the limit value of the force absorption and/or the deflection and the measured or determined force absorption and/or deflection. In one example, the information can be a difference formed from the maximum force absorption and the measured force absorption. In a further example, the information can be a color value, a geometric object, a text output or a combination thereof, which, for example, encodes the measured force absorption, the maximum force absorption or a difference formed from the measured force absorption and the maximum force absorption. For example, a volume element or a plurality of volume elements of the tissue can be marked via a red coloring or an exclamation mark in order to alert the operator of the robot to a local exceeding of the limit value of the force absorption in the volume element or the plurality of volume elements. In a further example, the information that the permissible deflection of a volume element or a plurality of volume elements of the tissue has been exceeded can be output in the form of a force feedback, such as, for example, a vibration of the robot's remote control. In this case, the robot and/or the remote control are embodied to output the force feedback. The information can further be a control command that terminates a movement of the catheter. It is conceivable that, for outputting a control command, the computing unit has a controller or a micro-controller, which transmits the control command to the robot and/or the robot's guide unit via an analog or digital signal.

The computing unit can furthermore be embodied to determine the information on the force absorption and/or the deflection of the volume element of the tissue and transmit it to the display unit. The information on the force absorption and/or the deflection of the volume element of the tissue position is preferably allocated information and/or a coordinate, which enables a spatial assignment of the information to a contrast of the first image data and/or the third image data. The computing unit can in particular be configured to register the information on the force absorption and/or the deflection of the volume element of the tissue with the first image data and/or the third image data and transmit it to the display unit.

Outputting the information on the force absorption and/or the deflection of the volume element of the tissue and the registration of this information with the third image data advantageously enables the operator of the robot to be informed about the current state of stress of the tissue. Further, outputting force feedback to the operator or a control command to the guide unit when a limit value is exceeded advantageously enables perforation of the tissue or a vascular rupture to be avoided.

The computer program product according to at least one embodiment of the invention can be loaded directly into a memory of the computing unit of the system and has program code segments in order to execute a method according to at least one embodiment of the invention when the computer program product is executed in the computing unit of the system. The computer program product according to at least one embodiment of the invention enables the method according to at least one embodiment of the invention to be executed in a quick, identically repeatable and robust manner.

The computer program product is configured such that it can execute the method steps according to at least one embodiment of the invention via the computing unit. Herein, the computing unit must in each case fulfill the requisite conditions such as, for example, an appropriate random-access memory, an appropriate graphics card or an appropriate logic unit so that the respective method steps can be executed efficiently.

The computer program product is for example stored on a computer-readable medium or held on a network, a server or a cloud from where it can be loaded into the processor of a local computing unit, which can be embodied as an independent system component or as a part of the first imaging modality, the second imaging modality, the display unit or the robot. Furthermore, control information for the computer program product can be stored on an electronically readable data carrier. The control information of the electronically readable data carrier can be embodied such that it can carry out a method according to at least one embodiment of the invention when the data carrier is used in a computing unit of a combined imaging device. Examples of electronically readable data carriers are a DVD, a magnetic tape or a USB stick on which electronically readable control information, in particular software, is stored. When this control information is read from the data carrier and in stored in a controller and/or computing unit of a system according to at least one embodiment of the invention, all the embodiments according to the invention of the above-described methods can be carried out.

FIG. 1 shows an embodiment of a system 1 according to the invention, which in the present case has an X-ray apparatus 2 with a C-arm 6 on which an X-ray tube 7 and an X-ray detector 8 are arranged opposite one another. In the embodiment shown, the X-ray apparatus 2 constitutes the second imaging modality, which is embodied to acquire first image data and/or third image data of the tissue. In the example shown, the tissue constitutes a vessel 32 of the medical target object, in this case a patient 15. The X-ray apparatus 2 is aligned such that a target region 9 of a patient 15 positioned on a patient table 17 can be recorded. Herein, the target region 9 constitutes a section of the tissue, which is positioned between a starting point 30 and a target region 31 of the catheter 34. In the example depicted, the target region 9 corresponds to the current imaging region of the X-ray apparatus 2. The C-arm 6 can be used to move the X-ray apparatus 2 formed by the X-ray tube 7 and the X-ray detector 8 into different recording positions with respect to a patient 15 lying on the patient table 17 in order to move the imaging region of the X-ray apparatus 2 along the vessel 32 as the catheter 34 advances from the starting point 30 to the target region 31.

The X-ray apparatus 2 further has a control unit 4 embodied to control the X-ray apparatus 2. The tasks of the control unit 4 can in particular comprise the adjustment of various imaging parameters, the coordination of various image recording and image processing steps and the transmission of first image data or third image data to the computing unit 40 of the system 1. The system 1 furthermore comprises a display unit 41 and an operator control unit 42 in order to enable interaction with an operator. In the present embodiment, the computing unit 40 is integrated in a computer or a PC and connected to the display unit 41 and the operator control unit 42. Herein, the computing unit 40, the display unit 41 and the operator control unit 42 form a user interface 23 via which a method according to the invention can, for example, be started, ended and/or parameterized.

In the example shown, the operator is a treating physician 29 who is located at a distance 3 from the X-ray tube 7 and operates the robot 50 via the remote control 52. Herein, the robot 50 has the guide unit 51 which moves the catheter 34, for example in dependence on a control command of the remote control 52, along a planned path 80 in the vessel 32.

In the embodiment of the system 1 according to the invention shown, the first imaging modality is an ultrasound apparatus 60. The ultrasound apparatus 60 has an ultrasound probe 61, which is embodied to record first elasticity data and/or second elasticity data of the tissue. For this purpose, the ultrasound probe is positioned on the target region 9 of the patient 15 in which a tip of the catheter 34 is located. The ultrasound apparatus 60 can, for example, be embodied as a 3D ultrasound elastography device or a 2D ultrasound elastography device. The ultrasound apparatus 60 is preferably embodied to support common sonography methods, such as, for example, one-dimensional Doppler methods, two-dimensional Doppler-methods or Duplex methods.

In the example shown, the ultrasound apparatus 60 and the X-ray apparatus 2 are connected to the computing unit 40 via the signal connections 43a and 43b. The signal connections 43a and 43b enable bidirectional exchange of analog and/or digital information. Preferably, at least digitized tissue information, such as, for example, tissue information of the first image data from the X-ray apparatus 2 and the first elasticity data from the ultrasound apparatus 60 is transmitted to the computing unit 40. However, it is likewise conceivable for the computing unit 40 to define the acquisition of first image data, second image data, third image data, first elasticity data and/or second elasticity data and to transmit a control command for carrying out a corresponding measuring method to the control unit 4 of the X-ray apparatus 2 and/or the ultrasound apparatus 60. The control unit 4 of the X-ray apparatus 2 and the ultrasound apparatus 60 are preferably configured to define corresponding parameter sets, such as, for example, a plurality of imaging parameters, based on such a control command and to implement them in the measurement method. The computing unit 40 is also connected to the robot 50 via the signal connection 43d. The signal connection 43d can also be configured to enable bidirectional exchange of analog and/or digital information between the computing unit 40 and the robot 50. Examples of such information constitute control commands, positioning instructions, tissue information or measured values of force absorption of a sensor (not shown) of the catheter.

Figure 2:
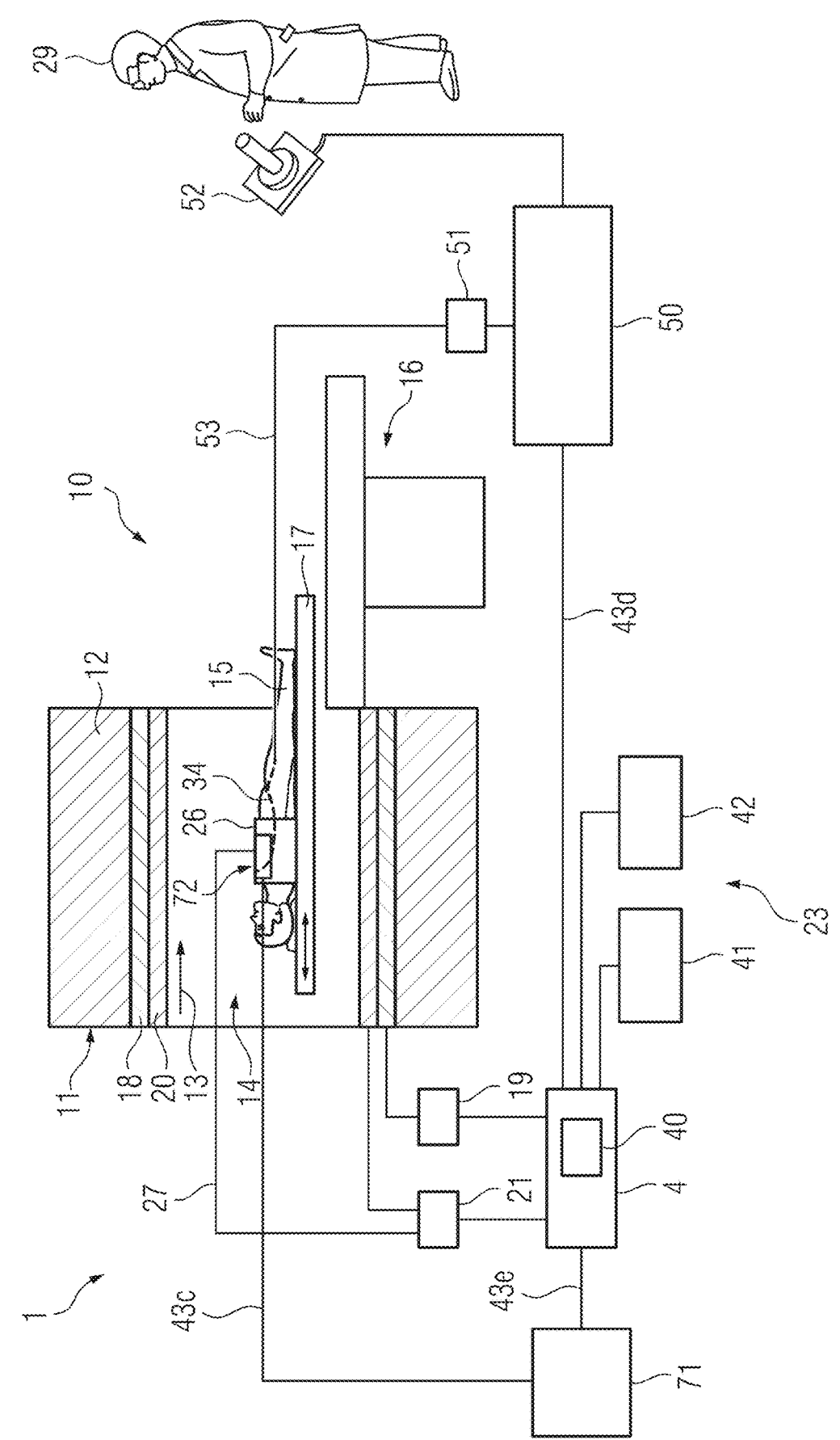
FIG. 2 shows an embodiment of a system according to the invention.

FIG. 2 shows a further embodiment of the system 1 according to the invention. In this example, the first imaging modality corresponds to the second imaging modality, which constitutes a magnetic resonance apparatus 10 with an active driver apparatus 71 and a passive driver 72 for performing an elastography measurement.

The magnetic resonance apparatus 10 comprises a magnetic unit 11 with, for example, a permanent magnet, an electromagnet or a superconducting main magnet 12 for generating a strong and in particular homogeneous main magnetic field 13. The magnetic resonance apparatus 10 also comprises a patient-receiving region 14 for receiving a patient 15. In the present example embodiment, the patient-receiving region 14 is cylindrical and surrounded by the magnetic unit 11 in a circumferential direction. However, in principle, embodiments of the patient-receiving region 14 that differ from this example are likewise conceivable.

The patient can be positioned in the patient-receiving region 14 via a patient support apparatus 16 of the magnetic resonance apparatus 10. For this purpose, the patient support apparatus 16 has a patient table 17 that can be moved within the patient-receiving region 14. The magnetic unit 11 furthermore has a gradient coil 18 for generating magnetic field gradients used for spatial encoding during imaging. The gradient coil 18 is actuated via a gradient control unit 19 of the magnetic resonance apparatus 10. The magnetic unit 11 can furthermore comprise a radio-frequency antenna embodied in the present example embodiment as a body coil 20 permanently integrated in the magnetic resonance apparatus 10. The body coil 20 is configured to excite nuclear spins located in the main magnetic field 13 generated by the main magnet 12. The body coil 20 is actuated by a radio-frequency unit 21 of the magnetic resonance apparatus 10 and radiates radio-frequency signals into a region of interest substantially formed by a patient-receiving region 14 of the magnetic resonance apparatus 10. The body coil 20 is furthermore embodied to receive magnetic resonance signals.

To control the main magnet 12, the gradient control unit 19 and to control the radio-frequency unit 21, the magnetic resonance apparatus 10 has a control unit 4. The control unit 4 is embodied to control the performance of a sequence, such as, for example, an imaging gradient echo sequence or a turbo spin echo sequence. In the example shown, the control unit 4 also comprises the computing unit 40, which is also embodied to evaluate digitized magnetic resonance signals acquired during the magnetic resonance examination. The computing unit 40 and the control unit 4 are, for example, embodied to transmit digital and/or analog information via the signal connection 43e to the active driver apparatus 71 and the robot 50. Such information can in particular comprise control commands which are implemented by the active driver apparatus 71 and the robot 50. The computing unit 40 and the control unit 4 can likewise be embodied to receive signals and/or information from the active driver apparatus 71 via the signal connection 43e.

Moreover, the magnetic resonance apparatus 10 comprises a user interface 23 with a signal connection to the control unit 4. The display unit 41 of the user interface 23 is preferably configured to display parameter sets, first image data, second image data, third image data, first elasticity data, second elasticity data, limit value distributions and/or navigation plans on a monitor of the user interface 23 for the treating physician 29. Furthermore, the user interface 23 comprises an operator control unit 42 via which parameter sets of the magnetic resonance apparatus 10 can be adapted by the treating physician 29. The user interface 23 can furthermore provide a possibility for starting, ending or parameterizing the method according to the invention.

The magnetic resonance apparatus 10 furthermore comprises a local coil 26 which is positioned on the patient 15 and transmits magnetic resonance signals from a body region of the patient 15 to the magnetic resonance apparatus 10. The local coil 26 has an electrical connecting lead 27 that provides a signal connection to corresponding receiver channels of radio-frequency unit 21 and the control unit 22. The receiver channels filter and digitize the signal received by the local coil 26 and transfer the data to the computing unit 40, which derives an image or a spectrum from the data and makes it available to the treating physician 29 via the display unit 41. The passive driver 72, which, for example, emits acoustic sound waves into the tissue of the patient 15, can be mechanically connected to the local coil 26. In the example shown, the actuation of the passive driver 72 via the active driver apparatus 71 takes place via the signal connection 43*c*.

In the example depicted, the computing unit 40 and the control unit 4 are connected to the robot 50 via the signal connection 43*d*. It is conceivable that, if a maximum force absorption and/or a permissible deflection of the tissue is exceeded, the computing unit 40 outputs a control command, which is transmitted to the robot 50 via the control unit 4 and the signal connection 43*d*. Such a control command can, for example, comprise a limitation of the movement of the catheter 34 in one spatial direction or the termination of the movement of the catheter 34. In one embodiment, the catheter 34 has a sensor for determining the application of force on the tissue of the patient 15. The measured application of force can, for example, be transmitted to the robot 50 via the connecting lead of the catheter 53. It is conceivable for the robot 50 to independently limit a movement of the catheter 34 in dependence on the measured application of force. It is likewise conceivable for the measured application of force to be transmitted to the computing unit 40 via the signal connection 43*d*. In one embodiment, the computing unit 40 is embodied to transmit the measured application of force to the display unit 41 for visualization. The computing unit 40 can furthermore be embodied to output a control command to the robot 50 which limits a movement of the catheter in dependence on the measured application of force.

The computing unit 40 depicted in the embodiments in FIG. 1 and FIG. 2 is further embodied to transmit information, such as, for example, tissue information from the first image data, the second image data, the third image data, the first elasticity data, the second elasticity data and the limit value distribution and/or the navigation plan, to the display unit 41. Herein, the information can in particular be present in a suitable data format, such as, for example, a DICOM format. It is conceivable that the display of the information can be adapted and/or changed by the treating physician 29 via the operator control unit 42, for example in order to change color values of the elasticity values registered in the first image data or to select a two-dimensional image section from the three-dimensional first image data. The system components in FIG. 1 and FIG. 2 are further electrically and mechanically connected to one another via the signal connections 43*a-e*. However, it is likewise conceivable for the system components to have network interfaces that enable wireless communication between the system components. It is furthermore conceivable for the information exchange between the system components to take place partly via analog signals (for example in the case of control commands) and partly by wireless means (for example in the case of first image data).

Figure 3:
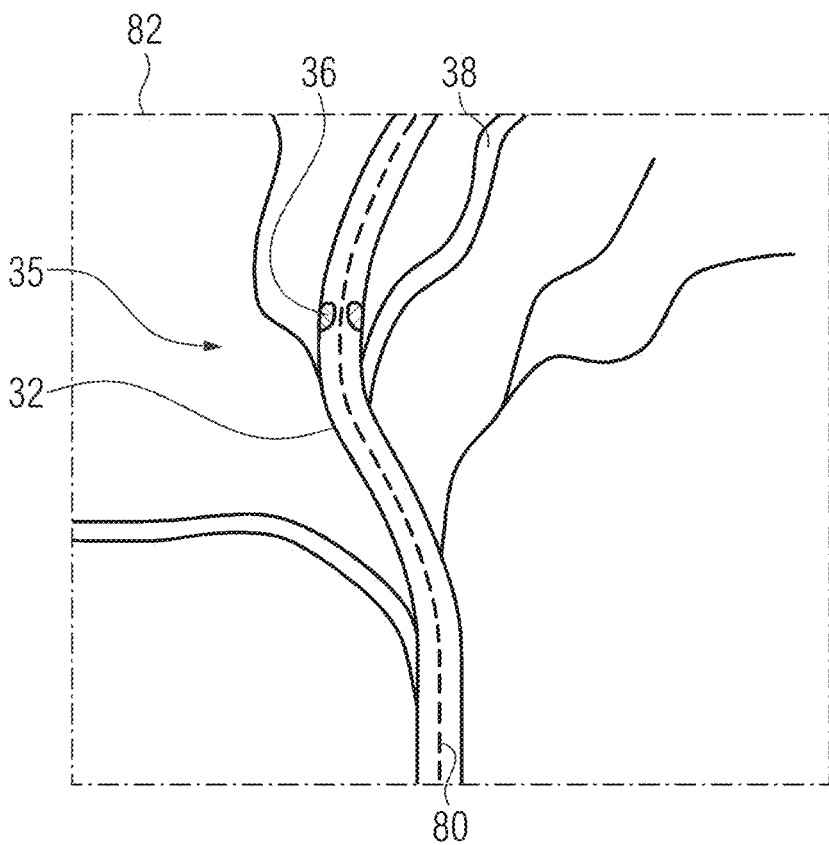
FIG. 3 shows a schematic depiction of a possible navigation plan in a vessel of a medical target object.

FIG. 3 shows a schematic depiction of a possible navigation plan 82 in the tissue of a patient 15. Herein, the navigation plan 82 has a two-dimensional section of the first image data with spatially resolved contrasts of the anatomical structures of the patient 15. The section of first image data shows the vessel 32 through which the catheter 34 is to be navigated. In addition, the navigation plan 82 comprises coordinates of a planned path 80 through the vessel 32. Herein, the planned path 80 is registered with the section of first image data such that the planned path 80 can be depicted as a line relative to the anatomical structures of the patient 15 on the display unit 41. In the section of first image data, the vessel 32 is embedded in the surrounding tissue 35, which can influence the properties, in particular the elastic properties, of the vessel wall of the vessel 32.

In the example shown, the vessel 32 has a deposit 36 positioned along the planned path 80 of the catheter 34 on the vessel wall. It is conceivable for the deposit 36 to constitute a target region 31 of the catheter 34. In this case, the catheter 34 can, for example, be embodied as a balloon catheter, which is inflated in the direction of flow of the blood behind the deposit 36 in order to remove the deposit 36 with the catheter 34 from the vessel 32. The catheter 34 can likewise be embodied to remove the deposit by exerting a mechanical force. It is further conceivable for the deposit 36 to be positioned on the way to a target region 31 and for it to be necessary to reduce or avoid mechanical interaction between the catheter 34 and the deposit 36. In this case, the planned path 80 of the navigation plan 82 can be embodied such that the catheter 34 passes or circumvents the deposit 36 with minimal interaction, for example by navigation into a branch 38 of the vessel 32.

Figure 4:
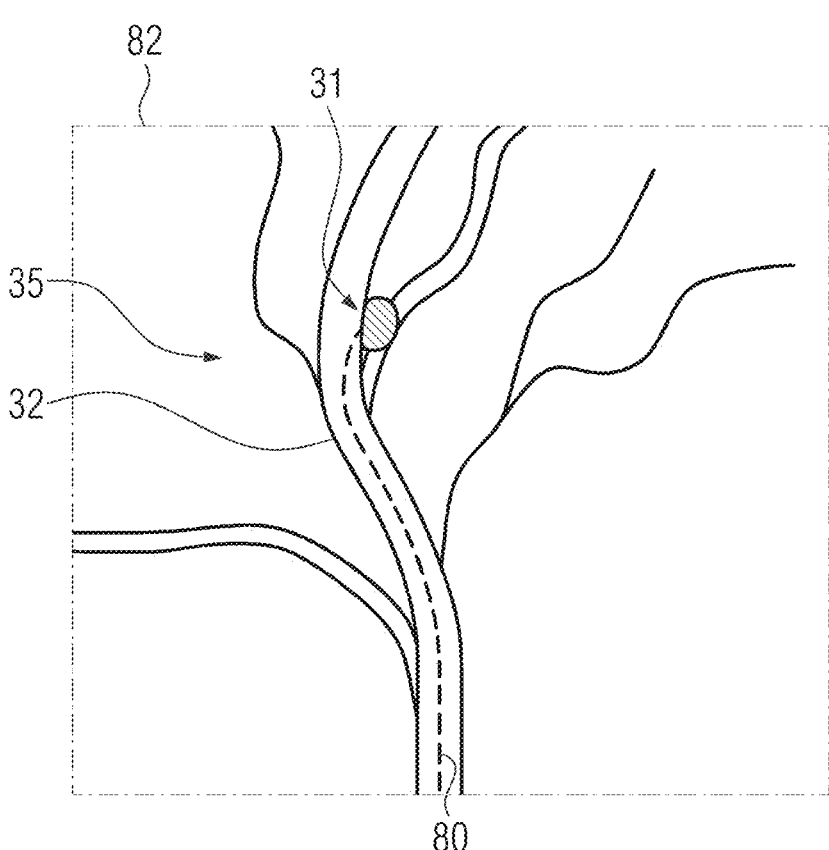
FIG. 4 shows a schematic depiction of a possible navigation plan in a vessel of a medical target object.

FIG. 4 shows a further schematic depiction of a possible navigation plan 82 in the tissue of the patient 15. Here, the target region 31 is a vascular aneurysm which is to be treated by the intervention. Herein, treatment can, for example, comprise embolization with the aid of coils and/or an application of a stent with the aid of the catheter 34.

Figure 5:
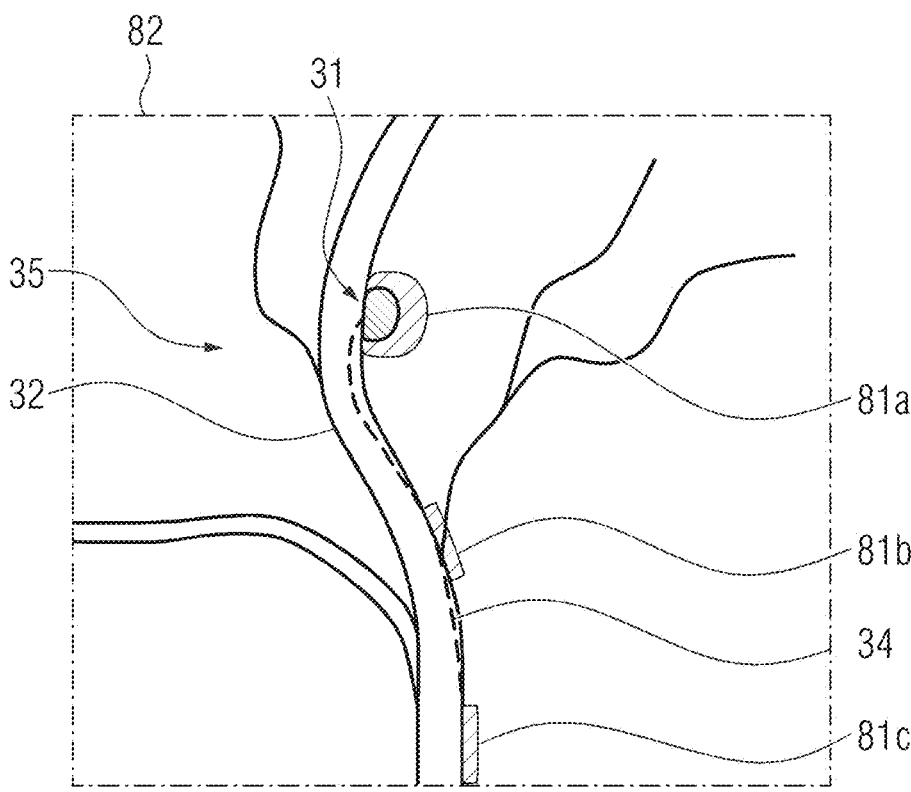
FIG. 5 shows a schematic depiction of a possible navigation plan in a vessel of a medical target object.

FIG. 5 shows a navigation plan 82 registered with a two-dimensional section of third image data with spatially resolved contrasts of anatomical structures of the patient 15. The third image data comprises real-time images of the tissue of the patient 15 and the catheter 34 in the vessel 32. The catheter 34 has contact points with the vessel wall of the vessel 32 at a plurality of locations at which a force is transmitted from the catheter 34 to the vessel wall. Here, the vessel wall of the aneurysm which may be exposed to increased force during embolization with coils may be of particular importance.

To estimate the stress on the vessel wall, the two-dimensional section of third image data is additionally registered in the navigation plan 82 with information on the force absorption and/or the deflection of the vessel wall, which is visualized in the form of objects 81*a* to 81*c* on the display unit 41. In the example shown, an object 81*a-c* is depicted at each point of contact between the catheter 34 and the vessel wall of the vessel 32 indicating the amount of force applied and the difference from the maximum force absorption of the limit value distribution. Herein, the amount of force absorption is encoded by a size of the object 81*a-c*, while the difference from the maximum force absorption is encoded by a color value of the object 81*a-c*. In the example shown, the color of the objects 81*b* and 81*c* can, for example, be green in order to signal the application of a low force by the catheter 34 on the vessel wall that does not locally exceed the maximum force absorption. On the other hand, the color of the object 81*a* can be orange if the filling of the aneurysm with coils exerts a locally increased pressure on the vessel wall of the aneurysm. If it is detected that the maximum force absorption of a volume element is exceeded, the computing unit 40 can output a signal that causes force feedback to the remote control 52 of the treating physician 29 and/or immediately terminates a movement of the catheter 34.

Figure 6:
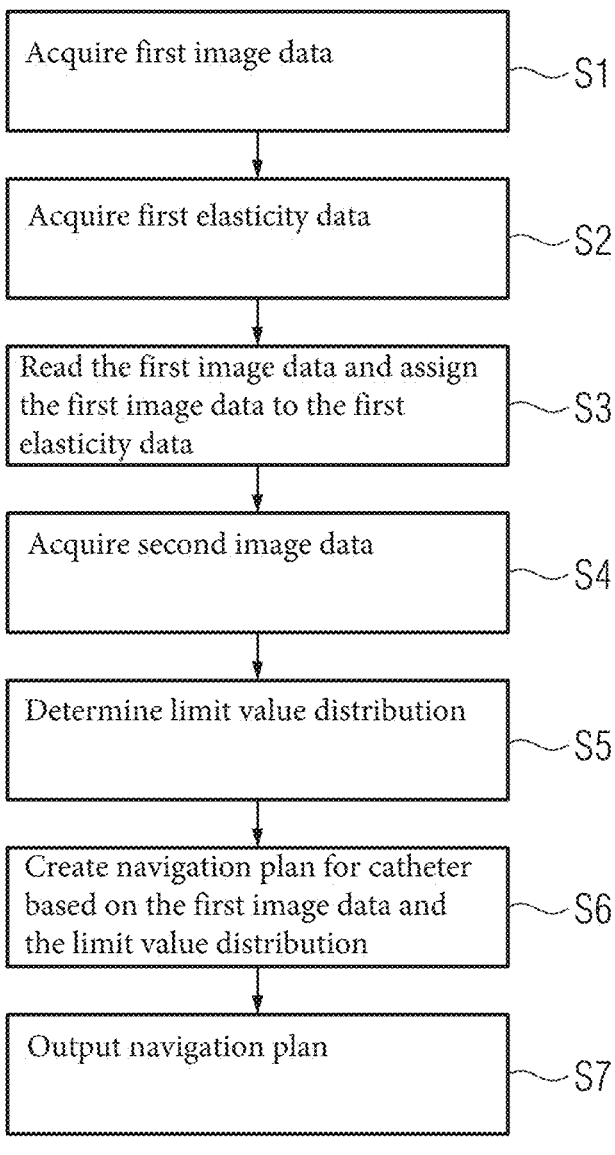
FIG. 6 shows a possible flow chart for a method according to an embodiment of the invention.

FIG. 6 shows a possible flow chart of the method according to an embodiment of the invention for creating the navigation plan 82 for the catheter 34 in the tissue in dependence on the limit value distribution.

In an optional step S1 of the method, the first image data of the tissue is acquired via the first imaging modality and/or the second imaging modality. Herein, the acquisition of the first image data can, for example, take place with a magnetic resonance apparatus 10, an X-ray apparatus 2, an ultrasound apparatus 60 or the like. In the following embodiment of the method, the tissue constitutes a vessel 32 with the surrounding tissue 35. The medical target object, for example a patient 15, is preferably positioned in a predetermined position on a patient table 17 of the first imaging apparatus and/or the second imaging apparatus such that a position of the patient 15 on the recording of the first image data matches a position of the patient 15 on the recording of first elasticity data, second elasticity data, second image data and/or third image data. During the acquisition of the first image data, preferably, three-dimensional tissue information on the anatomical structures in the tissue 35 of the patient 15 is recorded. This three-dimensional tissue information is, for example, contrasts or gray-scale values assigned to position information or coordinates of volume elements of the tissue via tuples, vectors or a matrix. The parameter set of the first imaging modality and/or the second imaging modality is preferably set such that anatomical and/or pathological structures relevant for the navigation of the catheter 34 are recorded with high contrast. Such anatomical or pathological structures can in particular comprise deposits 36 on a vessel wall, vascular aneurysms and vascular ruptures.

In a further step (S2) of the method, first elasticity values of the tissue are acquired via the first imaging modality, wherein the first elasticity data comprises spatially resolved elasticity values of volume elements of the tissue. The first imaging modality can, for example, be a magnetic resonance apparatus 10 or an ultrasound apparatus 60 embodied to measure elasticity values. During the acquisition of the first elasticity data, the patient 15 is preferably in a predetermined position on the patient table 17 of the first imaging modality. Herein, the predetermined position of the patient 15 can match the predetermined position of the patient 15 during the recording of the first image data.

During the acquisition of the first image data, spatially resolved elasticity values of volume elements of the tissue are recorded via the first imaging modality. The elasticity data preferably constitutes three-dimensional tissue information in which the elasticity values are assigned to position information or coordinates of volume elements of the tissue via tuples, vectors or a matrix.

In a further step (S3), the first image data is read in and assigned to the first elasticity data, wherein an elasticity value of a volume element of the tissue is allocated to a volume element of the tissue of the first image data. Herein, first image data is preferably read in via the computing unit 40, which receives the first image data from the first imaging modality and/or the second imaging modality or reads the first image data from a database, such as, for example, a physical memory or cloud storage. The computing unit 40 then assigns the first elasticity values to the first image data. Herein, the first image data and the first elasticity data preferably have a common coordinate system so that the elasticity values of the volume elements of the tissue can be assigned to the gray-scale values of the volume elements of the tissue based on coordinates. However, it is likewise conceivable for the assignment of the first image data and the first elasticity data to take place via a transform, iteration method and/or further mathematical operations. Herein, the elasticity values are preferably registered with the first image data. This can mean that the elasticity values are, for example, superimposed on the first image data in the form of a colored marking or pattern. The target region 31 and/or another anatomical structure relevant for the creation of the navigation plan 82, such as, for example, a deposit 36 or an aneurysm, are preferably already contrasted in the first image data.

Furthermore, patient information is preferably read in when the first image data is read in. The patient information can in particular comprise the treatment history, medical history, age, gender and weight of the patient 15.

In an optional step S4 of the method, second image data of the tissue is acquired via the first imaging modality or the second imaging modality, wherein, during the acquisition of the second image data, a parameter set of the first imaging modality or the second imaging modality is selected such that a travel speed and/or a pressure gradient of a fluid in the vessel 32 of the tissue can be determined, wherein the navigation plan 82 is created in dependence on information on the travel speed and/or the pressure gradient of the fluid in the vessel 32 of the tissue. The first imaging modality or the second imaging modality can, for example, be a magnetic resonance apparatus 10, an ultrasound apparatus 60, a computed tomography apparatus or the like embodied to measure flow rates. During the acquisition of the second image data, the patient 15 is preferably in a predetermined position on the patient table 17 of the first imaging modality or the second imaging modality. Herein, the predetermined position of the patient 15 can match the predetermined position of the patient 15 during the recording of the first image data and/or the first elasticity data.

Herein, a parameter set can comprise different imaging parameters of the first imaging modality or the second imaging modality or also a contrast agent dose. During the acquisition of the second image data, spatially resolved speed values and/or speed vectors of the blood in the vessel 32 of the tissue are measured. It is conceivable that, before the creation of the navigation plan 82, for the computing unit 40 to first assign the second image data to the first image data. Herein, the first image data and the second image data preferably have a common coordinate system so that the speed values of the volume elements of the vessel 32 can be assigned to the gray-scale values of the volume elements of the vessel 32. However, it is likewise conceivable for the assignment of the first image data and the second image data to take place via a transform, an iteration method and/or further mathematical operations. Herein, the speed values are preferably registered with the first image data. This can mean that the speed values are superimposed on the first image data, for example in the form of a color marking or a pattern.

In a further step S5 of the method, the limit value distribution is determined at least in dependence on the first elasticity data and assigned to the first image data, wherein a limit value of a volume element of the tissue is allocated to a volume element of the tissue of the first image data. The determination of the limit value distribution can, for example, take place via a biomechanical model and/or a model-based approach. The biomechanical model can, for example, be based on a numerical solution of a (differential) equation system with which properties of the tissue can be determined at discrete support points. Herein, the support points can match a finite number of equidistantly distributed sub-bodies of the tissue. Alternatively or additionally to the biomechanical model, it is possible to use a model-based approach in order to determine the limit value distribution. It is conceivable for the model-based approach to have a function that adapts the maximum force absorption and/or the permissible deflection of the tissue in dependence on empirical data via curve fitting. Herein, the empirical data can, for example, correlate the weight, age, gender or pre-existing condition of the patient 15 and the type, slice thickness (first image data) or an elasticity value of a volume element of the tissue or the like and provide the relationship between these variables in the form of a function. Of course, other approaches as described above are also conceivable.

The limit value distribution is then assigned to the first image data, wherein a limit value of a volume element of the tissue is allocated to a volume element of the tissue of the first image data. Herein, the limit value distribution and the first image data preferably have a common coordinate system so that the limit values of the volume elements of the tissue can be assigned to the contrasts or gray-scale values of the volume elements of the tissue. However, it is likewise conceivable for the assignment of the limit value distribution and the first image data to take place via a transform, iteration method and/or further mathematical operations. Herein, the limit values are preferably registered with the first image data. This can mean that the limit values are superimposed on the first image data, for example, in the form of a text window, a colored marking of a pattern or the like.

In a further step S6 of the method, the navigation plan 82 of the catheter 34 in the vessel 32 is created at least in dependence on the first image data and the limit value distribution. During the creation of the navigation plan 82, a plurality of tuples, a plurality of vectors or a matrix is for example applied which assign the coordinates and/or position information of the volume elements of the tissue to the gray-scale values or contrasts of the first image data and the limit values. Herein, it is further conceivable for the spatially resolved speeds and/or pressure gradients of the second image data to be assigned to the coordinates and/or position information of the volume elements of the tissue. The gray-scale values or contrasts of anatomical structures can furthermore also originate from first image data in which deposits 36 or accumulations of fluid have a particularly high contrast.

The navigation plan 82 further has a planned path 80 on which the catheter 34 is guided through the vessel 32. The planned path 80 is, for example, determined using optimization methods or iteration methods which reduce or minimize stress on the vessel walls of the vessel 32 caused by the catheter 34 along the planned path 80. In one embodiment, the planned path 80 is, for example, stored as a sequence of direction vectors. In an alternative embodiment, the planned path 80 is stored as a sequence of coordinates and/or a sequence of positioning instructions. The sequence of coordinates and/or the sequence of positioning instructions can then be output together with the navigation plan 82 or separately therefrom.

In an optional step S7, the navigation plan 82 of the catheter 34 is output. An output can, for example, comprise a visualization of a two-dimensional or three-dimensional image section with contrasts of the first image data, elasticity values of the first elasticity data and the planned path 80 on the display unit 41. Herein, the plurality of tuples, vectors or the matrix of the navigation plan 80 can be transformed by the computing unit 40 into a multidimensional virtual image of the vessel 32 and/or the surrounding tissue 35 from which three-dimensional or two-dimensional images and/or image sections with any orientations can be created. Herein, the elasticity values, speed values and/or limit values are, for example, registered with the images and/or can be selectively faded in or faded out by the operator as a layer or slice.

In one embodiment, the elasticity values, the speed values, the limit values and the planned path of the catheter 34 through the vessel 32 are superimposed or registered with third image data of the tissue so that the treating physician 29 can follow the progress of the intervention on the display unit 41 based upon real-time images.

In a further embodiment, during the output of the navigation plan 82, control commands are also output, based upon which the catheter 34 is moved in the vessel 32. Herein, the sequence of coordinates and/or the sequence of positioning instructions of the navigation plan 82 can be transmitted as control commands to the robot 50 and/or the guide unit 51. The control commands can subsequently be converted into a movement of the catheter 34 via a drive of the robot 50 or the guide unit 51.

A method described herein can also be present in the form of a computer program which implements the method on the computing unit 40 when it is executed on the computing unit 40. Likewise, an electronically readable data carrier (not depicted) can be present with electronically readable control information stored thereupon which comprises at least one described computer program and is embodied such that it carries out a described method when the data carrier is used in the computing unit 40.

Although the invention was illustrated and described in more detail by the preferred example embodiment the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for creating a navigation plan for a catheter in tissue, the method comprising:

acquiring first elasticity data of the tissue via a first imaging modality, the first elasticity data including spatially resolved elasticity values of volume elements of the tissue;

reading in first image data and assigning the first elasticity data to the first image data, an elasticity value of a volume element of the volume elements of the tissue being allocated to a volume element of the tissue of the first image data;

determining a limit value distribution based on the first elasticity data and assigning the limit value distribution to the first image data, the limit value distribution including spatially resolved limit values for at least one of a maximum force absorption or a permissible deflection of the volume elements of the tissue, wherein, for at least one volume element of the volume elements of the tissue, a limit value of the limit value distribution for the volume element of the volume elements of the tissue is allocated to a corresponding volume element of the tissue of the first image data; and creating the navigation plan for the catheter in the tissue at least in dependence on the first image data and the limit value distribution to improve navigation planning and reduce a risk of complications when navigating the catheter in the tissue.

2. The method of claim 1 further comprising:

acquiring the first image data of the tissue via at least one of the first imaging modality and a second imaging modality, the first imaging modality and the second imaging modality including at least one of a magnetic resonance apparatus, a computed tomography apparatus, an ultrasound apparatus, or an x-ray apparatus.

3. The method of claim 2, wherein a parameter set of at least one of the first imaging modality and the second imaging modality is selected during the acquiring of the first image data such that a deposit in a vessel of the tissue is detected, and wherein the creating of the navigation plan takes place in dependence on information on the deposit in the vessel.

4. The method of claim 2, wherein a parameter set of at least one of the first imaging modality and the second imaging modality is selected during the acquiring of the first image data such that an accumulation of fluid in the tissue is localized, and wherein the creating of the navigation plan takes place in dependence on information on the accumulation of the fluid in the tissue.

5. The method of claim 2, further comprising:

acquiring second image data of the tissue via the first imaging modality or the second imaging modality, wherein a parameter set of the first imaging modality or the second imaging modality is selected during the acquiring of the second image data such that a travel speed of a fluid in a vessel of the tissue is determined, and wherein the creating of the navigation plan takes place in dependence on information on the travel speed of the fluid in the vessel of the tissue.

6. The method of claim 1, wherein the determining of the limit value distribution takes place via at least one of a biomechanical model of the tissue and a model-based approach.

7. The method of claim 1, further comprising:

outputting the navigation plan for the catheter.

8. The method of claim 2, wherein the determining of the limit value distribution takes place via at least one of a biomechanical model of the tissue and a model-based approach.

9. The method of claim 2, further comprising:

outputting the navigation plan for the catheter.

10. A robot for navigating a catheter into a target region of tissue of a medical target object, the robot comprising:

a guide unit, embodied to change at least one of a position and an orientation of the catheter, and the catheter being controllable via the guide unit in dependence on a navigation plan, creating the navigation plan including:

acquiring first elasticity data of the tissue via a first imaging modality, the first elasticity data including spatially resolved elasticity values of volume elements of the tissue;

reading in first image data and assigning the first elasticity data to the first image data, an elasticity value of a volume element of the volume elements of the tissue being allocated to a volume element of the tissue of the first image data;

determining a limit value distribution based on the first elasticity data and assigning the limit value distribution to the first image data, the limit value distribution including spatially resolved limit values for at least one of a maximum force absorption or a permissible deflection of the volume elements of the tissue, wherein, for at least one volume element of the volume elements of the tissue, a limit value of the limit value distribution for the volume element of the volume elements of the tissue is allocated to a corresponding volume element of the tissue of the first image data; and creating the navigation plan for the catheter in the tissue at least in dependence on the first image data and the limit value distribution to improve navigation planning and reduce a risk of complications when navigating the catheter in the tissue.

11. The robot of claim 10, wherein the robot is configured to navigate the catheter into the target region automatically in dependence on the navigation plan.

12. A system, comprising:

a robot for navigating a catheter into a target region of tissue of a medical target object, the robot including a guide unit, embodied to change at least one of a position and an orientation of the catheter, and the catheter being controllable via the guide unit in dependence on a navigation plan, creating the navigation plan including:

acquiring first elasticity data of the tissue via a first imaging modality, the first elasticity data including spatially resolved elasticity values of volume elements of the tissue;

reading in first image data and assigning the first elasticity data to the first image data, an elasticity value of a volume element of the volume elements of the tissue being allocated to a volume element of the tissue of the first image data;

determining a limit value distribution based on the first elasticity data and assigning the limit value distribution to the first image data, the limit value distribution including spatially resolved limit values for at least one of a maximum force absorption or a permissible deflection of the volume elements of the tissue, wherein, for at least one volume element of the volume elements of the tissue, a limit value of the limit value distribution for the volume element of the volume elements of the tissue is allocated to a corresponding volume element of the tissue of the first image data; and creating the navigation plan for the catheter in the tissue at least in dependence on the first image data and the limit value distribution to improve navigation planning and reduce a risk of complications when navigating the catheter in the tissue;

at least one of the first imaging modality and a second imaging modality; and a computing unit, having a signal connection to at least one of the robot, the first imaging modality and the second imaging modality, embodied to determine the limit value distribution at least in dependence on the first elasticity data and the first image data and to create the navigation plan.

13. The system of claim 12, wherein at least one of the first imaging modality and the second imaging modality are embodied to acquire second elasticity data during navigation of the catheter into the target region and wherein the computing unit is embodied to update the limit value distribution and the navigation plan in dependence on the second elasticity data.

14. The system of claim 12, wherein the robot comprises a sensor, including a signal connection to the computing unit, configured to acquire a force absorption of a volume element of the volume elements of the tissue during navigation of the catheter into the target region and wherein the computing unit is configured to at least one of output information and limit movement of the catheter upon the limit value of the force absorption of a volume element of the volume elements of the tissue being exceeded.

15. The system of claim 12, wherein at least one of the first imaging modality and the second imaging modality are embodied to acquire third image data during navigation of the catheter into the target region and wherein the computing unit is configured to determine at least one of a force absorption and a deflection of a volume element of the volume elements of the tissue in dependence on the third image data and at least one of output information and limit movement of the catheter upon the limit value of at least one of the force absorption and the deflection of a volume element of the volume elements of the tissue being exceeded.

16. The system of claim 13, wherein the computing unit is configured to output information on at least one of force absorption and deflection of a volume element of the volume elements of the tissue during navigation of the catheter into the target region.

17. A non-transitory computer readable medium storing program code segments for executing the method of claim 1 when the program code segments are executed via at least one processor.

* * * * *